United States Patent [19]

Schopflin et al.

[11] 4,155,991

[45] * May 22, 1979

[54] VAGINAL RING

[75] Inventors: Gisela Schopflin; Gerhard Laudahn; Barbara Muhe; Heidemarie Hartmann; Fred Windt, all of Berlin, Fed. Rep. of Germany

[73] Assignee: Schering Aktiengesellschaft, Berlin and Bergkamen, Fed. Rep. of Germany

[*] Notice: The portion of the term of this patent subsequent to Mar. 15, 1994, has been disclaimed.

[21] Appl. No.: 774,170

[22] Filed: Mar. 3, 1977

Related U.S. Application Data

[62] Division of Ser. No. 623,487, Oct. 17, 1975, Pat. No. 4,012,496.

[30] Foreign Application Priority Data

Oct. 18, 1974 [DE] Fed. Rep. of Germany ....... 2450107
Aug. 21, 1975 [DE] Fed. Rep. of Germany ....... 2537585

[51] Int. Cl.² .................. A61K 9/00; A61K 31/74
[52] U.S. Cl. ........................ 424/15; 128/130; 128/260
[58] Field of Search .............. 128/260, 130; 424/15, 424/19-22, 28

[56] References Cited

U.S. PATENT DOCUMENTS

| | | | |
|---|---|---|---|
| 3,527,210 | 9/1970 | Towns | 128/130 |
| 3,545,439 | 12/1970 | Duncan | 128/130 |
| 3,659,597 | 5/1972 | Wolfors | 128/130 |
| 3,744,489 | 7/1973 | Munro | 128/130 |
| 3,908,646 | 9/1975 | Ansari | 128/130 |
| 3,911,911 | 10/1975 | Scommegna | 128/130 |
| 3,920,805 | 11/1975 | Roseman | 424/15 |
| 4,012,496 | 3/1977 | Schopflin et al. | 424/15 |
| 4,012,497 | 3/1977 | Schopflin | 424/22 |
| 4,034,749 | 7/1977 | Von Kesseru et al. | 128/130 |
| 4,043,339 | 8/1977 | Roseman | 128/260 |

FOREIGN PATENT DOCUMENTS

| | | | |
|---|---|---|---|
| 2158226 | 5/1973 | Fed. Rep. of Germany | 424/22 |
| 2445971 | 4/1976 | Fed. Rep. of Germany | 128/260 |
| 2450107 | 4/1976 | Fed. Rep. of Germany | 128/130 |
| 7415908 | 6/1975 | Netherlands | 128/130 |
| 7512254 | 4/1976 | Netherlands | 128/130 |
| 1412970 | 11/1975 | United Kingdom | 128/130 |

OTHER PUBLICATIONS

Chem. Abstr. 79 #45823t (1973) of Schopflin et al., Ger. Off. 2,158,226, May 24, 1973.
Chem. Abstr. 84 #79719g (1976) of Schopflin et al., Brit. 1,412,970, Nov. 5, 1975.
Chem. Abstr. 85 #37243n (1976) of Schopflin, Ger. Off. 2,445,971, Apr. 8, 1976.
Chem. Abstr. 84 #95619e (1976) of Schering A/G, Neth. Appl. 74 15,908, Jun. 10, 1975.
Chem. Abstr. 85 #182419d (1976) of Schering A/G, Neth. Appl. 75 12,254, Apr. 21, 1976.

Primary Examiner—Shep K. Rose
Attorney, Agent, or Firm—Millen & White

[57] ABSTRACT

A composite vaginal ring containing a safe and effective amount of a pharmaceutically active medicament, which comprises:
(a) a major supporting vaginal ring consisting essentially of a physiologically acceptable synthetic resin and having at least a portion of the annular surface thereof adapted to mate with corresponding minor, medicament-containing vaginal ring segment; and
(b) at least one minor, medicament-containing vaginal ring segment adapted to mate with the modified annular surface of said major supporting vaginal ring and consisting essentially of a safe and effective amount of a pharmaceutically active amount of a nonionic, lipophilic drug dissolved or uniformly suspended in an elastomeric, cross-linked LTV linear dimethylpolysiloxane resin.

19 Claims, 16 Drawing Figures

VAGINAL RING

This is a division of application Ser. No. 623,487 filed Oct. 17, 1975, now U.S. Pat. No. 4,012,496.

CROSS-REFERENCE TO RELATED APPLICATIONS

Details regarding the preparation of LTV elastomer drug excipients can be found in copending, commonly assigned U.S. patent application Ser. No. 444,886 filed Feb. 22, 1974, now abandoned the contents of which are incorporated by reference herein.

BACKGROUND OF THE INVENTION

This invention relates to a vaginal ring containing active medicinal agents, especially estrogens or progestogens alone or in combination.

Vaginal rings containing progestationally active steroid hormones or a combination of progestationally and estrogenically effective medicinal agents for preventing conception with or without antiovulatory activity are advantageous whenever formulations of drugs for peroral administration, which contain these active agents, are contraindicated. Vaginal rings furthermore have the advantage of liberating women from a compulsory daily ingestion of tablets. These rings constitute annularly shaped articles which can be introduced into the vagina in a simple manner and which are well tolerated by female patients. As compared to conventional intrauterine pessaries and subdermally administered capsules, these rings have the further advantage that they can be removed and reinserted by the female patient herself at any time.

Vaginal rings made of a synthetic resin, especially silicone elastomers obtained from RTV (room temperature vulcanizing) silicone rubber two-component compositions, e.g. as described in Contraception 8:651 (1973) or from hot-vulcanized silicone rubber products as described in Steroids 21:325 (1973) and which contain active medicinal agents such as steroid hormones, are known per se, e.g. see Fertil. Steril. 21:99 (1970); Amer. J. Obstet. Gynecol. 113:927 (1972); Contraception 8:561 (1973); DOS [German Laid-Open Application] 1,900,196; etc. The active medicinal agent is released from the synthetic resin carrier over a prolonged period of time and is resorbed by the vaginal mucosa.

The steroid hormones contained in the conventional vaginal rings are exclusively those having a progestational effect. Depending on the release rate and amount of progestationally active agent, protection against conception is attained by the use of these rings either with or without attendant antiovulatory activity.

Heretofore known contraceptives in the form of vaginal rings, however, exhibit many known disadvantages. They are produced, inter alia, from RTV silicone rubber two-component compositions, the poor mechanical properties of which are notorious and must first be improved by the addition of fillers. These fillers, however, can disadvantageously influence the release of the medicinally active agent from the vaginal ring. Several conventional vaginal rings are manufactured by vulcanizing suspensions of the medicinal agent in RTV silicone rubber two-component compositions in appropriate molds. The active medicinal agents are released from this type of vaginal ring during the period of application in quantities which are greatly reduced in the course of time as has been reported in Contraception 8:561 (1973).

Considerable differences in the dosage of the active medicinal agents result perforce in qualitative and quantitative differences in the biological and/or contraceptive effect, as well as in the type and extent of undesired side effects during the period of application of the vaginal rings. Known vaginal rings which contain the medicinal agent as a homogeneous suspension in the synthetic resin base have a total weight of about 6.0–15.0 g. If the active medicinal agent is to be released from these vaginal rings in an adequate amount throughout the period of administration, they must contain about 5–30% by weight of the active medicinal agent. This content of effective agent in the drug formulation is uneconomically high as related to the amount of active medicinal agent which is actually released during the period of use. Heretofore, no suitable process has been known for adjusting the level of the desired active drug release rate for a certain active medicinal agent from vaginal rings made of silicone elastomers.

Previously known vaginal rings have been manufactured in part on the basis of synthetic resins which are not entirely physiologically harmless. Thus, RTV silicone rubber two-component compositions containing tin compounds as vulcanization accelerators are utilized for the manufacture of vaginal rings, but such vulcanization accelerators have a toxic effect on the living organism as has been reported in Amer. J. Obstet. Gynecol. 113:927 (1972).

Also known are relatively stiff vaginal rings provided with a metallic spring, similar to a pessary used for the treatment of a prolapse. During their use, erosion of the mucosa can occur in the zone of the posterolateral vaginal vault; see J.A.M.A. 208:949 (1969). British Pat. No. 1,264,732 describes devices consisting of a capsule containing the active medicinal agent on a plastic ring of silicone rubber. However, such devices are poorly suited for mass production due to their construction. Also, these rings lack practicality in their usage because the inward capsule containing the active medicinal agent hinders that the inner ring lies close to the cervix wall and this implies the risk of its dammage, what can be the cause of an increased expulsion rate.

Accordingly, there is still need to solve the problem of providing vaginal rings containing an active medicinal agent which release the active agents over a prolonged period of time, e.g. at least several weeks, regularly and in a uniform quantity required for attaining the desired biological effect, and to overcome the aforedescribed disadvantages inherent in conventional vaginal rings. The present invention fills such needs.

OBJECTS OF THE INVENTION

Accordingly, it is a general object of this invention to provide sustained release pharmaceutical compositions in the form of a vaginal ring.

Another object of this invention is to provide a convenient and highly adaptable drug implant for use in female animals which exhibits a uniform rate of drug release over a prolonged period of time.

A further object of this invention is to provide a vaginal ring adapted to receive an optionally detachable sustained release pharmaceutical composition.

An additional object of this invention is to provide a vaginal ring having sustained release of estrogen or progesterone hormonal activity.

A more particular object of this invention is to provide contraceptive and/or antiprotozoal vaginal rings which exhibit a sustained release of effective medicaments over a prolonged period of time.

Yet another object of this invention is to provide a medicated pessary.

Upon study of the specification and appended claims, further objects and advantages of this invention will become apparent to those skilled in the art.

SUMMARY OF THE INVENTION

Briefly, the above and other objects, features and advantages of the present invention are attained in one aspect thereof by providing a composite vaginal ring containing a safe and effective amount of a pharmaceutically active medicament, which comprises:

(a) a major supporting vaginal ring consisting essentially of a physiologically acceptable synthetic resin and having at least a portion of the annular surface thereof adapted to mate with corresponding minor, medicament-containing vaginal ring segment; and (b) at least one minor, medicament-containing vaginal ring segment adapted to mate with the modified annular surface of said major supporting vaginal ring and consisting essentially of a safe and effective amount of a pharmaceutically active amount of a nonionic, lipophilic drug dissolved or uniformly suspended in an elastomeric, cross-linked LTV linear dimethylpolysiloxane resin.

BRIEF DESCRIPTION OF THE DRAWINGS

The above features will become more fully apparent to those skilled in the art to which this invention pertains from the following Detailed Description, taken in conjunction with the annexed Drawings wherein.

DETAILED DISCUSSION

The above and other problems of the prior art are solved in accordance with the present invention by mounting on a supporting ring made of a synthetic resin one or two rings or ring sections which contain an active medicinal agent and are made of a silicone elastomer synthetic resin.

A preferred embodiment of the vaginal ring of this invention consists of a supporting ring having one or two annular continuous, pocket-like indentations adapted to receive rings which fit into these recesses, these rings containing an active medicinal agent and being made of an LTV silicone elastomer.

This vaginal ring according to the invention is composed of the actual synthetic-resin supporting ring with one or two recesses and an inner and/or outer ring containing an active medicinal agent which is fitted into the pocket-like recesses of the supporting ring.

The drug-containing rings preferably have a circular cross section. The cross section, however, can also be of the shape of a circular segment. The dimensions of the supporting ring and of the drug-containing rings are selected so that the contact points of the outer edge and the inner edge, respectively, of the supporting ring with the drug-containing ring lie above the center line of the drug-containing ring in case of a circular cross section or above the center line of the circle forming the segment in case of a cross section shaped like a circular segment. Thus, a favorable fixation of the drug-containing rings in the pocket-like recesses of the supporting ring is attained.

Figure 1:
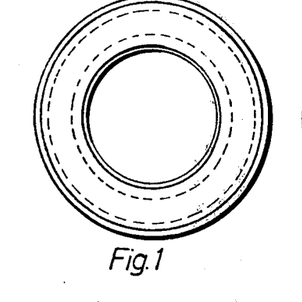
FIGS. 1-3 show top views of vaginal rings according to this invention.
Figure 2:
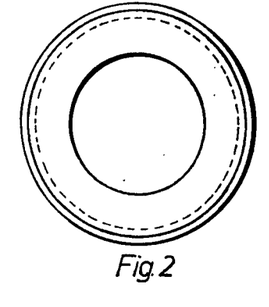
Figure 3:
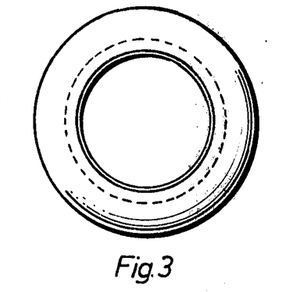
Figure 4:
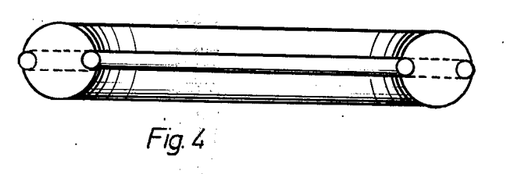
FIG. 4 shows a cross section through the vaginal ring having an inner ring and an outer ring both of circular cross section inserted therein.
Figure 4A:
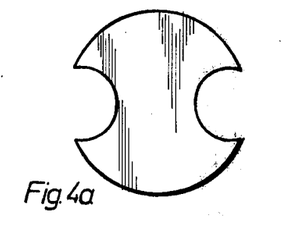
FIG. 4a shows an enlarged partial cross section of the supporting ring shown in FIG. 4.
Figure 5:
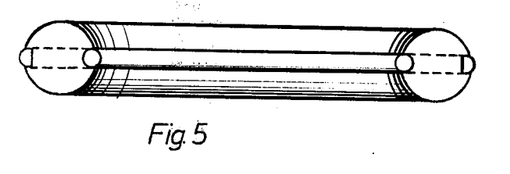
FIG. 5 shows a cross section through a vaginal ring with an inner ring having a circular cross section and an outer ring having a circular-segment-shaped cross section.
Figure 5A:
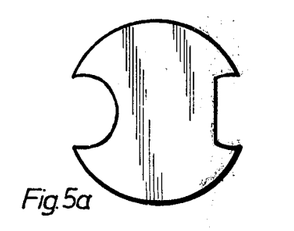
FIG. 5a shows an enlarged partial cross section of the supporting ring of FIG. 5.
Figure 6:
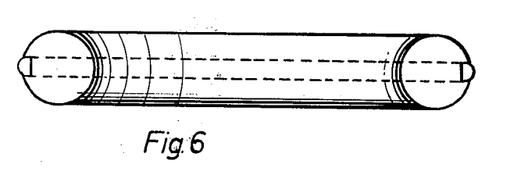
FIG. 6 shows a cross section through a vaginal ring having an outer ring with a cross section in the shape of a circular segment.
Figure 6A:
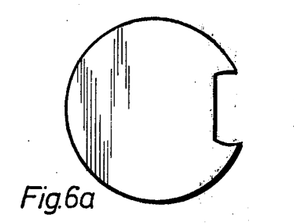
FIG. 6a shows an enlarged partial cross section of the supporting ring of FIG. 6.
Figure 7:
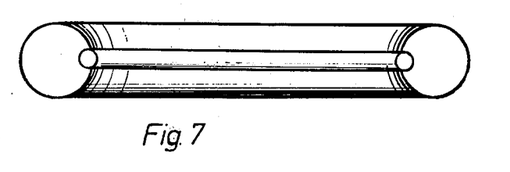
FIG. 7 shows a cross section through a vaginal ring with an inner ring having a circular cross section.
Figure 7A:
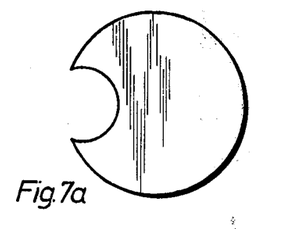
FIG. 7a shows an enlarged partial cross section of the supporting ring of FIG. 7.
Figure 8:
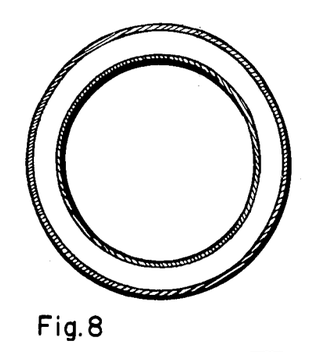
FIG. 8 shows a schematic top view of a vaginal ring with a drug-containing layer continuously applied on the inside and outside.
Figure 8A:
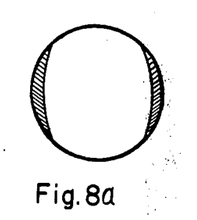
FIG. 8a, as a supplement, shows an enlarged partial cross section of the vaginal ring of FIG. 8.
Figure 9:
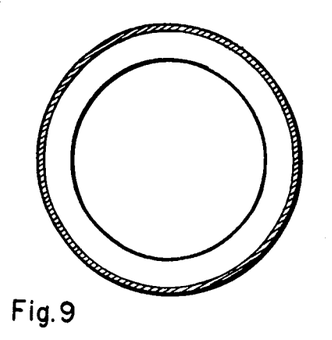
FIG. 9 shows a schematic top view of a vaginal ring having a drug-containing layer extending along the outer perimeter.
Figure 10:
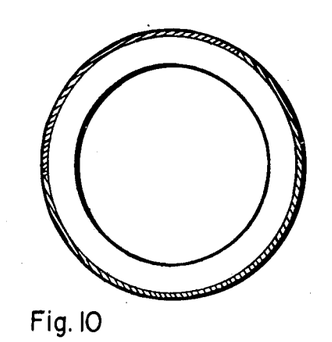
FIG. 10 is a schematic top view of a vaginal ring wherein two drug-containing layers are applied in succession in a section-wise manner along the outer perimeter.
Figure 11:
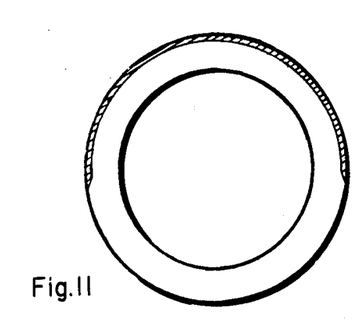
FIG. 11 shows a schematic top view of a vaginal ring wherein the drug-containing layer is applied to only a portion of the outer edge of the supporting ring.

One additional embodiment is a vaginal ring having an outer ring which has a circular cross section, e.g. as shown in the right hand side of FIG. 4a.

The supporting ring, in this embodiment, can consist of any kind of physiologically acceptable synthetic resin, as long as it possesses sufficient strength and elasticity. Suitable such synthetic resins are well known in the art and include but are not limited to organopolysiloxane elastomers, e.g. LTV dimethylpolysiloxane elastomer, hot-vulcanized dimethylpolysiloxane elastomers, polyamides, natural and synthetic rubber, polyesters, polytetrafluoroethylene and polyethylenes which are molded to the shaped article in a conventional manner, e.g. by injection-molding or casting.

Another preferred embodiment resides in applying rings which contain the active medicinal agent and are made on the basis of LTV silicone elastomer to a supporting ring made of LTV silicone elastomer by vulcanizing. This vaginal ring according to the present invention is composed of the following parts:

(a) The actual supporting ring with one or two drug-containing layers applied by vulcanization to the inside edge and/or to the outside edge of the supporting ring; and (b) The layers containing the active medicinal agent having a cross section in the shape of a circular segment. The dimensions of the supporting ring and of the drug-containing rings vulcanized thereon are preferably chosen so that the vulcanized-on layers are not in contact on the outer and/or inner edge of the supporting ring. The drug-containing layers can surround and- /or encompass the entire supporting ring or can be vulcanized thereon in partial sections.

The vaginal rings of the present invention have an average size of 0.5-20 cm., the particular size being dependent on the species for utilization of the ring, e.g. for smaller mammals, such as dogs, the ring size will be smaller than in the case of larger mammals such as horses and cows. In vaginal rings for use in women, the outer diameter is about 5-10 cm., and in the case of Rhesus monkeys, for example, about 2-3 cm. The diameter of such ring cross sections is generally 5-15 mm., preferably 7-10 mm.

The supporting ring and the drug-containing rings and/or the layers vulcanized thereon are produced on the basis of conventional LTV silicone elastomers. Organopolysiloxane two-component molding compositions of the LTV type (low temperature vulcanizing type) and components of these compositions are known, for example, from DAS's (German Published Applications) Nos. 1,171,641 and 1,900,969; DOS (German Unexamined Laid-Open Application) No. 1,940,124; U.S. Pat. Nos. 2,823,218, 3,159,601, 3,159,662 and 3,220,972.

The following LTV silicone elastomer compositions, described in detail in copending, commonly assigned U.S. patent applications Ser. No. 444,886 filed Feb. 22, 1974 now abandoned and Ser. No. 616,001 filed Sept. 23, 1975, now U.S. Pat. No. 4,012,497 the contents of which are incorporated by reference herein, are especially preferred for at least the medicament-containing vaginal ring segment in accordance with the present invention:

LTV SILICONE ELASTOMER A

A nontoxic pharmaceutical composition adapted for implantation into a human or animal body to provide a constant, uniform drug release rate over a time interval of several months or years, being substantially free of peroxide, acetic acid and metal salts of carboxylic acids and consisting essentially of a homogeneous mixture of:

(a) 85-95, preferably 89-91, parts by weight of an LTV linear dimethylpolysiloxane resin containing 0.05-0.5 molar percent of methylvinylsiloxane units, having a molecular weight of 20,000-50,000 and containing an average of 1.58-2.02 monovalent hydrocarbon residues per silicone atom;

(b) correspondingly 15-5, preferably 11-9, parts by weight of a cross-linking composition consisting essentially of a dimethylpolysiloxane cross-linking agent substantially free of methylvinylsiloxane units, having a molecular weight of 500-1000 and containing 1-3 Si-H bonds per molecule;

(c) a catalytic amount of a noble-metal based cross-linking catalyst; and (d) a pharmaceutically active amount of a nonionic, lipophilic drug dissolved or uniformly suspended in said composition.

LTV SILICONE ELASTOMER B

This composition is similar to LTV Silicone Elastomer A but contains preferably 85-89 parts by weight of component (a); preferably 5-6 parts by weight of component (b); together with 5-10 parts by weight of a dimethylpolysiloxane resin having a molecular weight of 10,000-40,000 and having 0.2-1.5 molar percent methylvinylsiloxane units as an auxiliary cross-linking agent.

LTV SILICONE ELASTOMER C

This composition is preferably used with medicaments having an unsaturated structure in the molecule, and comprises:

(a) 20-100 parts by weight of an organopolysiloxane having a viscosity of 500-200,000 centistokes (at 25° C.) and having the general formula wherein R is lower alkyl (preferably methyl) and/or aryl of up to 10 carbon atoms, and n is an integer from 200-1600;

(b) 0-50 parts by weight of an organopolysiloxane copolymer consisting essentially of:

(i) $(R')_3SiO_{0.5}$ units, (ii) $(R')_2(Vi)SiO_{0.5}$ units, and (iii) $SiO_2$ units, wherein Vi is a vinyl group and R' is a monovalent organic residue which does not contain any unsaturated groups, and at least 50% of R' is methyl, and wherein the ratio of a+b/c is 0.4-1.5 (preferably 0.6-1.0) and the ratio of b/c is 0.02-0.5 (preferably 0.05-0.15);

(c) 5-15 parts by weight of an organohydrogen polysiloxane of the general formula wherein R" is a monovalent organic residue which has no unsaturated groups; a and b are each positive numbers; the ratio of a:b is 0.5-10 (preferably 1.0-5); the sum of a+b is 1-2.5; and wherein at least three hydrogen atoms bound to different Si atoms are present per molecule; which component contains 50-500 molar percent, based on the unsaturated end groups in components (a) and (b) of vinyl groups attached to SiH; and (d) a catalytic amount of platinum or a platinum compound.

The alkyl and/or aryl residues R contained in component (a) are of up to 10 carbon atoms. Examples in this connection include but are not limited to methyl, ethyl, propyl, isopropyl, butyl, octyl, tert.-amyl, cyclopentyl, cyclohexyl, phenyl, napthyl, tolyl, xylyl, benzyl, chlorophenyl, cyanomethyl and 3,3,3-trifluoropropyl residues.

The residues R' and R" contained in components (a) and (b) are each independently alkyl residues of up to 8 carbon atoms, preferably of up to 3 carbon atoms, e.g. methyl, ethyl and n-propyl.

Components (a), (b) and (d) constitute one component of the LTV organopolysiloxane two-component molding composition, while component (c) constitutes the second component having a cross-linking effect.

Component (a) and/or the mixture of components (a), (b) and (c) or (a), (b), (c) and (d) can contain metallic ions, e.g. copper (II) ions for delayed curing at room temperature in an amount of 2.61 to 75 parts by weight of metallic ions per part by weight of platinum.

Although the vulcanization of the organopolysiloxane molding compositions in the presence of the noble metal catalyst can take place at room temperature, vulcanization at a slightly elevated temperature is especially advantageous. The vulcanizing period of the catalyzed mixture is 1–6 hours at 60°–120° C. To initiate the vulcanization, the mixture can also be heated for a short time to a higher temperature, e.g. to 150° C. for a period of 1–10 minutes, but maximally 15 minutes.

The platinum component (d) of the molding composition can actually be used in one of the conventional forms catalyzing the reaction between silicon-linked hydrogen residues and silicon-linked vinyl residues. Examples in this connection are metallic platinum per se; platinum on support materials, e.g. silica gel or carbon powder; hexachloroplatinic acid and platinum salts, such as platinum carbonyl dichloride $PtCOCl_2$ and platinum dicarbonyl dichloride $Pt(CO)_2Cl_2$; etc. All of these platinum compounds are usable as catalysts. However, pure hexachloroplatinic acid has the disadvantage that it shows a relatively sparse solubility in organosilicon compounds containing silane groupings. Platinum compounds used in the solid form as catalysts cause the cross-linking reaction to take place very slowly and with poor controllability, just as the reaction as such can also be interrupted more readily than can be expected with the use of comparable catalysts in solution. Therefore, hexachloroplatinic acid is preferably used as the catalyst while dissolved in isopropanol, and $PtCOCl_2$ and $Pt(CO)_2Cl_2$ are used as the catalyst while dissolved in a diorganopolysiloxane containing 10–15 molar percent of vinyl groups. In this connection, at least 0.1 part by weight of platinum must be used per 1 p.p.m. of (a) and (b). Since impurities in the molding compositions can poison such small amounts of catalyst, 10–40 p.p.m. of platinum is preferably employed, although larger quantities of platinum do not impair the reaction.

A special embodiment of the vaginal ring according to this invention resides in that the same LTV silicone elastomer is employed for the supporting ring as well as for the drug-containing ring of synthetic resin.

In one embodiment of the supporting ring utilized for the vaginal ring of this invention, the supporting ring consists of a foamed silicone elastomer with closed cell pores. For this purpose, volatile agents such as, for example, hydrocarbons such as pentane or heptane and halogenated hydrocarbons, such as methylene chloride, monofluorodichloromethane, trichlorofluoromethane and trichlorofluoroethane, etc. are introduced in finely dispersed form into the mixture to be vulcanized and evaporated during the vulcanization.

The vulcanizates obtained from these organopolysiloxane two-component molding compositions are inactive with respect to nonionic, lipophilic active medicinal agents, nonpoisonous for the living organism, compatible, and are not absorbed by the living organism.

The effective agents contained in the drug-containing rings are preferably effective agents having a hormonal activity, e.g. estrogens and progestogens. Such compounds are well known in the art and include but are not limited to 3-methoxy-17α-ethynyl-1,3,5(10)-estratrien-17-ol (mestranol); 3-hydroxy-1,3,5(10)-estratrien-17-one (estrone); 17β-estradiol; estriol; ethynylestradiol; 4-pregnene-3,20-dione (progesterone); d-13-ethyl-17α-ethynyl-17β-hydroxy-4-gonen-3-one (d-norgestrel) and the esters thereof; 17α-ethynyl-19-nortestosterone (norethisterone) and the esters thereof; 6-chloro-17-hydroxy-1α,2α-methylenepregna-4,6-diene-3,20-dione (cyproterone) and the esters thereof; 19-norhydroxyprogesterone and the esters thereof; 6-chloro-17-acetoxy-pregna-4,6-diene-3,20-dione (chlormadinone acetate); 15,16α-methylene- and 15,16β-methylene-17β-hydroxy-18-methyl-17α-ethynyl-4-estren-3-one; 17α-acetoxy-6α-methylprogesterone (medroxy-progesterone acetate); 9β,10α-pregna-4,6-diene-3,20-dione (dydrogesterone); etc.

As the active medicinal agents, all those can actually be used which are nonionic and lipophilic. Accordingly, neuroleptics, such as butyrophenone derivatives, e.g. haloperidol, or bacteriostatics and/or fungistats, such as nystatin or metronidazole, are suitable for incorporation into the silicone elastomer.

The amount of active agent incorporated into the LTV silicone elastomer is generally 10–60% by weight, based on the total composition, and is dependent in individual cases on the specific active agent or active agent combination. Examples are the following total doses in milligrams:

|  | Useful | Preferred |
|---|---|---|
| Cyproterone acetate | 200–1000 | 250–750 |
| d-norgestrel | 100–500 | 200–400 |
| Ethynylestradiol | 20–100 | 25–50 |
| Estradiol | 20–90 | 25–50 |
| Mestranol | 50–100 |  |
| Ethynylnortestosterone acetate | 150–950 | 200–800 |
| Estrone | 10–80 |  |
| Estriol | 15–70 |  |
| Progesterone | 250–900 |  |
| Norethisterone | 100–600 | 200–500 |
| Cyproterone | 100–900 | 200–700 |
| Norhydroxyprogesterone | 250–950 |  |
| Chlormadinone acetate | 170–850 |  |
| 15,16α-Methylene- and 15,16β-methylene-17β-hydroxy-18-methyl-17α-ethynyl-4-estren-3-one | 50–750 | 100–500 |
| Dydrogesterone | 100–550 |  |
| Metronidazole | 300–950 |  |

Thus, it is readily possible for the outer ring to contain only a progestogen, whereas the inner ring contains an estrogen, or conversely. Progestogens or estrogens can be applied, for example, in combination with bactericides.

The total quantity of active agent in the LTV silicone elastomer is dimensioned so that a specific, constant amount per day is released over the desired time period. In detail, these amounts are, for example, in case of:

| | | |
|---|---|---|
| Cyproterone acetate | 300–1000 | μg./d. |
| d-Norgestrel | 30–250 | μg./d. |
| Ethynylestradiol | 30–60 | μg./d. |
| Estradiol | 20–150 | μg./d. |
| Mestranol | 20–100 | μg./d. |
| Ethynylnortestosterone acetate | 300–1000 | μg./d. |

One embodiment of the vaginal ring according to this invention resides in using same for the prevention of conception. A contraceptive effect on the basis of ovulation inhibition is attained over the period of application of the vaginal ring according to this invention if this ring releases, e.g. daily amounts of 130–250 μg. of ethynylestradiol or 800–1000 μg. of cyproterone acetate and 30–50 μg. of ethynylestradiol. Vaginal rings containing antiprotozoal agents in the drug-comprising inner or outer rings, e.g. metronidazole, and optionally estrogens are suitable in particular for the treatment of trichomoniasis. The active medicinal agent is incorporated into the LTV silicone elastomer base for producing the drug-containing ring. For this purpose, the active agent is comminuted and/or finely ground, optionally micronized; mixed with an LTV silicone elastomer two-component composition to form a suspension free of air bubbles; shaped into rings; and vulcanized by heating, preferably at 40°–120° C.

The drug-containing rings have, in the case of the outer ring, a diameter of 0.5–8.0 mm., preferably 1.5–5.0 mm., and in the case of the inner ring, a diameter of 0.3–2.0 mm., preferably 0.4–1.6 mm.

The drug-containing rings are built up entirely or partially according to the matrix principle. The drug-containing rings, however, can also consist of a core containing the active agent and an outer silicone elastomer shell of any desired layer thickness, low in active agent content; conversely, these rings can consist of a core element low in active agent content and surrounded by an elastomer layer containing the active medicinal agent. Such an envelope low in active medicinal agent over a core enriched in the active agent with a predominantly suspended active agent is obtained, for example by short-term extraction of the suspension vulcanizates containing the active medicinal agent with a suitable solvent, e.g. ethanol/water 1:1 (vol./vol.).

The rings containing the active medicinal agent are inserted in the pocket-like recesses of the supporting ring; glued optionally with the aid of catalyzed LTV silicone elastomer two-component composition and subsequently vulcanized to half the side of the recesses of the supporting ring, or they are molded onto the initially vulcanized supporting rings and the vulcanized completely together with the supporting ring.

The supporting ring, the drug-containing outer and-/or inner ring constitute, either put together and/or glued together, the actual vaginal ring.

To produce the drug-containing coating on the supporting ring, the active agent is likewise incorporated into the LTV silicone elastomer base. For this purpose, the active agent is finely ground, optionally micronized; mixed into a suspension with an LTV silicon elastomer two-component composition; applied in the form of a layer to the initally vulcanized supporting ring with the use of the multicomponent injection molding technique; and vulcanized by heating, preferably at 40°–120° C.

It can also be advantageous to combine the synthetic resin-active agent suspension with an auxiliary substance, such as, for example, a tenside, a defrother, a solubilizer, and/or a resorption-delaying agent in order to impart to the molded article any desired physical properties. Furthermore, however, inert auxiliary agents can also be used, such as highly disperse silicone dioxide, which impart to the ring the desired mechanical characteristics.

The drug-containing coatings, when they are vulcanized onto the outer edge of the supporting ring, have a layer thickness of 0.1–5.0 mm., preferably 0.5–3.0 mm. When they are vulcanized onto the inner edge of the supporting ring, the drug-containing coatings have a layer thickness of 0.1–3.0 mm., preferably 0.5–2.0 mm.

The drug-containing coatings are built up entirely or partially in accordance with the matrix principle.

Since no by-products are formed during the vulcanization of the LTV silicone elastomer two-component composition, a subsequent heat treatment of the cured product is superfluous.

The vaginal rings of this invention have the advantage that the active medicinal agents are released therefrom over a longer time period regularly and uniformly within the limits of the dosage required for the desired biological effect, e.g. for the inhibition of ovulation. Moreover, these vaginal rings have the advantage that the amount of active agent which must be incorporated into a single such contraceptive can be much lower than in the case of the conventional vaginal rings, since the medicament-containing surface thereof is in direct contact with the vaginal wall.

The vaginal rings of the present invention on the basis of LTV silicone elastomer do not crumble under mechanical stress. They cannot be damaged as readily during their introduction into the body as vaginal rings on the basis of RTV elastomers containing more or less defined mixtures of active fillers with the notorious, disadvantageous characteristics which they exert on the medicinal agent, which fillers must be incorporated to improve the mechanical properties.

With the aid of the vaginal ring according to this invention, many active medicinal agents can be successfully utilized which could not be used with the heretofore known and customary carrier materials in the conventional vaginal rings.

The vaginal rings producible in accordance with this invention can be sterilized in saturated, pressurized steam at 120° C. without incurring undesired changes during this step.

The following examples are to explain the present invention.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following examples, the temperatures are set forth uncorrected in degrees Celsius; unless otherwise indicated, all parts and percentages are by weight.

EXAMPLE 1

A supporting ring intended for receiving two drug-containing rings is injection-molded from a polyethylene-vinyl acetate copolymer ("ALATHON" E/VA 3170, DuPont & de Nemours) with the following dimensions: outer diameter of the supporting ring, 6 cm.; inner diameter of the supporting ring, 4.2 cm.; and spacing between the pocket-like recess for the outer ring and the pocket-like recess for the inner ring, 5.5 mm. The drug-containing outer ring has a diameter of 4 mm.; the drug-containing inner ring has a diameter of 0.5 mm. The vaginal ring has a ring cross section diameter of 10.1 mm.

The drug-containing outer ring with a diameter of 4 mm. is molded from a homogeneous suspension of 15.0 g. of d-norgestrel in 85.0 g. of the LTV organopolysiloxane two-component molding composition I and vulcanized by heating for two hours at 110° C. The LTV organopolysiloxane two-component molding composition $C_1$ comprises 75 parts by weight of a polydimethylsiloxane having bilateral vinyl end groups and a viscosity of 50,000 centistokes at 25° C.; 25 parts by weight of a copolymer composed of 40 molar percent $SiO_2$ units, 45 molar percent $(CH_3)_3SiO_{0.5}$ units and 15 molar percent $Vi(CH_3)_2SiO_{0.5}$ units; 8 parts by weight of an Si—H component comprising 16.6 molar percent $(CH_3)_3SiO_{0.5}$ units, 33.4 molar percent $(CH_3)_2SiO$ units and 50 molar percent $CH_3HSiO$ units; and 10 p.p.m. of platinum (based on the total mixture) in the form of a 2% solution of $H_2PtCl_6$ in isopropanol. The drug-containing inner ring is produced from a homogeneous suspension of 58.0 g. of ethynylestradiol in 42.0 g. of the LTV organopolysiloxane two-component molding composition $C_2$ by molding and two hours of vulcanizing at 105° C. The LTV organopolysiloxane two-component molding composition $C_2$ is composed of 85 parts by weight of a bilaterally vinyl-terminated polydimethylsiloxane having a viscosity of 1000 centistokes at 25° C.; 15 parts by weight of a copolymer having the composition of 40 molar percent $SiO_2$ units, 45 molar percent $(CH_3)_3SiO_{0.5}$ units and 15 molar percent $Vi(CH_3)_2SiO_{0.5}$ units; 4.5 parts by weight of an Si—H component containing 38 molar percent $SiO_2$ units, 29 molar percent $(CH_3)_3SiO_{0.5}$ units and 33 molar percent $(CH_3)_2HSiO_{0.5}$ units; and 10 p.p.m. of platinum (based on the total mixture) in the form of a 2% solution of $H_2PtCl_6$ in isopropanol.

EXAMPLE 2

A supporting ring is produced from dimethylpolysiloxane molding composition ("SILASTIC" 4600, Dow Corning) by molding, followed by 5 minutes of initial vulcanization at 150° C. and one hour of vulcanization at 120° C.; this supporting ring has the following dimensions: outer diameter, 6 cm.; inner diameter, 4.2 cm.; and spacing between the pocket-like recess for the outer ring and the pocket-like recess for the inner ring, 5.3 mm.

In this supporting ring are inserted a d-norgestrel-containing outer ring having a diameter of 4 mm. and a mestranol-containing inner ring having a diameter of 1 mm. The d-norgestrel-containing outer ring is prepared from a suspension of 20.0 g. of d-norgestrel and 18.0 g. of highly disperse silicon dioxide in 62.0 g. of the LTV organopolysiloxane two-component molding composition $C_3$ by molding and vulcanizing for two hours at 100° C. The LTV organopolysiloxane two-component molding composition $C_3$ is composed of: 75 parts by weight of a bilaterally vinyl-terminated polydimethylsiloxane having a viscosity of 1000 centistokes at 25° C.; 25 parts by weight of a copolymer comprised of 40 molar percent $SiO_2$ units, 45 molar percent $(CH_3)_3SiO_{0.5}$ units and 15 molar percent $Vi(CH_3)_2SiO_{0.5}$ units; 8 parts by weight of an Si—H component comprising 16.6 molar percent $(CH_3)_3SiO_{0.5}$ units, 33.4 molar percent $(CH_3)_2SiO$ units and 50.0 molar percent $CH_3HSiO$ units; 30 p.p.m. of platinum (based on the total mixture) in the form of a 1% solution of $Pt(CO)_2Cl_2$ in an open-chain dimethylpolysiloxane containing 12 molar percent vinyl groups; and 5 parts by weight, based on the platinum, of Cu(II) ions.

The mestranol-containing inner ring is prepared from a homogeneous suspension of 60.0 g. of mestranol in 40.0 g. of the LTV organopolysiloxane two-component molding composition $C_4$ by molding and vulcanizing for 40 minutes at 110° C. The LTV organopolysiloxane two-component molding composition $C_4$ comprises 75 parts by weight of a bilaterally vinyl-terminated polydimethylsiloxane having a viscosity of 1000 centistokes at 25° C.; 25 parts by weight of a copolymer composed of 40 molar percent $SiO_2$ units, 45 molar percent $(CH_3)_3SiO_{0.5}$ units and 15 molar percent $Vi(CH_3)_2SiO_{0.5}$ units; 8 parts by weight of an Si-H component comprising 16.6 molar percent $(CH_3)_3SiO_{0.5}$ units, 33.4 molar percent $(CH_3)_2SiO$ units and 50.0 molar percent $CH_3HSiO$ units; and 10 p.p.m. of platinum (based on the total mixture) in the form of a 2% solution of $H_2PtCl_6$ in isopropanol.

EXAMPLE 3

Supporting rings having the dimensions indicated in Example 2 are produced, according to the procedure described therein, from a homogeneous mixture of 35.0 g. of highly disperse silicon dioxide and 65.0 g. of resin-reinforced dimethylpolysiloxane molding composition ("SIL GEL" 2001, Wacker Chemie).

Vaginal rings are prepared with the use of these supporting rings by inserting and gluing drug-containing inner and outer rings having the dimensions described in Example 2.

The above-indicated catalyzed two-component composition is employed for gluing. The drug-containing outer ring is made from a suspension of 25.0 g. of micronized cyproterone acetate and 15.0 g. of highly disperse silicon dioxide in 60.0 g. of the LTV organopolysiloxane two-component molding composition $C_5$ by molding and vulcanizing for two hours at 115° C. The LTV organopolysiloxane two-component molding composition $C_5$ comprises 75 parts by weight of a bilaterally vinyl-terminated polydimethylsiloxane having a viscosity of 50,000 centistokes at 25° C.; 25 parts by weight of a copolymer composed of 40 molar percent $SiO_2$ units, 45 molar percent $(CH_3)_3SiO_{0.5}$ units and 15 molar percent $Vi(CH_3)_2SiO_{0.5}$ units; 8 parts by weight of an Si-H component containing 16.6 molar percent $(CH_3)_3SiO_{0.5}$ units, 33.4 molar percent $(CH_3)_2SiO$ units and 50 molar percent $CH_3HSiO$ units; and 35 p.p.m. of platinum (based on the total mixture) in the form of a 1.5% solution of $Pt(CO)_2Cl_2$ in a dimethylpolysiloxane containing 15 molar percent vinyl groups.

The drug-containing inner ring is made from a suspension of 20.0 g. of estradiol in the LTV organopolysiloxane two-component molding composition $C_6$ by molding and vulcanizing for two hours at 110° C.

The LTV organopolysiloxane two-component molding composition $C_6$ contains the following ingredients: 75 parts by weight of bilaterally vinyl-terminated polydimethylsiloxane having a viscosity of 50,000 centistokes at 25° C.; 25 parts by weight of a copolymer composed of 40 molar percent $SiO_2$ units, 45 molar percent $(CH_3)_3SiO_{0.5}$ units and 15 molar percent $Vi(CH_3)_2SiO_{0.5}$ units; 8 parts by weight of an Si-H component containing 16.6 molar percent $(CH_3)_3SiO_{0.5}$ units, 33.4 molar percent $(CH_3)_2SiO$ units and 50 molar percent $CH_3HSiO$ units; and 25 p.p.m. of platinum (based on the total mixture) in the form of a 2% solution of $Pt(CO)_2Cl_2$ in a dimethylpolysiloxane containing 10 molar percent vinyl groups.

EXAMPLE 4

Supporting rings having a diameter of 9 mm. with a spacing between the pocket-like recess for receiving the drug-containing outer ring and the pocket-like recess for the drug-containing inner ring of 5.3 mm. are manufactured from a homogeneous mixture of 30.0 g. of highly disperse silicon dioxide in a catalyzed LTV silicone elastomer base as a dimethylpolysiloxane casting composition ("SILOPREN" 0228, Bayer) by molding, initially vulcanizing for 5 minutes at 140° C. and completing the vulcanization at 120° C. for 120 minutes. These supporting rings are designed for receiving a d-norgestrel-containing outer ring having a diameter of 3.0 mm. and an estradiol-containing inner ring having a diameter of 1.0 mm. The vaginal ring has a diameter of its ring cross section of 10.3 mm. The d-norgestrel-containing outer ring is prepared from a suspension of 15.0 g. of micronized d-norgestrel and 20.0 g. of highly disperse silicon dioxide in 65.0 g. of the LTV organopolysiloxane two-component molding composition $C_4$ described in Example 2 by molding and vulcanizing for 2 hours at 110° C. The vulcanizates are extracted successively for 90 minutes with 96% ethanol, again for 30 minutes with 96% ethanol, for 60 minutes with 70% ethanol, and for 30 minutes with 50% ethanol at room temperature and are then air-dried. In this way, d-norgestrel-containing rings are obtained having an envelope of low d-norgestrel content surrounding a core enriched in d-norgestrel. The estradiol-containing inner ring is molded from a suspension of 35.0 g. of micronized estradiol in 65.0 g. of the LTV organopolysiloxane two-component molding composition $C_3$ described in Example 2 and vulcanized by heating for two hours at 100° C.

EXAMPLE 5

Supporting rings having the dimensions of Example 1 are produced from dimethylpolysiloxane molding composition (Dow Corning "SILASTIC" 4600) as indicated in Example 2. Vaginal rings are prepared by inserting the drug-containing outer and inner rings of Example 1 into these supporting rings.

EXAMPLE 6

Supporting rings having the dimensions set forth in Example 1 are injection-molded from a terephthalate basis thermoplastic polyether ester elastomer.

These supporting rings are designed for receiving a d-norgestrel-containing outer ring, as described in Example 2, and an ethynylestradiol-containing inner ring, as described in Example 1, which are inserted in the supporting ring.

EXAMPLE 7

Supporting rings having the dimensions described in Example 4 are made from a suspension of 32.0 g. of highly disperse silicon dioxide in the LTV organopolysiloxane two-component molding composition $C_4$ described in detail in Example 3, following the method indicated in Example 4.

The drug-containing outer rings are produced from a suspension of 35.0 g. of micronized ethynylnortestosterone acetate and 15.0 g. of highly disperse hydrophobic silicon dioxide in 50.0 g. of LTV organopolysiloxane two-component molding composition $C_3$ as described in Example 2 by molding and two hours of vulcanizing at 100° C. The drug-containing inner rings have the composition of the inner rings according to Example 3 and are manufactured analogously. The supporting ring, the drug-containing outer ring and the drug-containing inner ring are combined into a vaginal ring.

EXAMPLE 8

Supporting rings having a cross section diameter of 9 mm. with a spacing between the pocket-like recesses for receiving drug-containing outer and inner rings of 6.2 mm. are produced according to the method disclosed in Example 4 from a suspension of 28.0 g. of highly disperse silicon dioxide and 5.0 g. of barium sulfate in 67.0 g. of catalyzed LTV silicone elastomer two-component composition ("SILOPREN" 0839, Bayer). The supporting rings are designed to receive a d-norgestrel-containing outer ring having a cross section shaped like a circular segment and having a diameter of 2.5 mm. and to receive an ethynylestradiol-containing inner ring having a diameter of 0.5 mm.

The d-norgestrel-containing outer ring is prepared from a suspension of 40.0 g. of d-norgestrel in 60.0 g. of the LTV organopolysiloxane two-component molding composition $C_1$ as described in Example 1, by molding and vulcanizing for 90 minutes at 110° C.

The ethynylestradiol-containing inner rings are obtained from 55.0 g. of ethynyestradiol and 45.0 g. of the LTV organopolysiloxane two-component molding composition $C_3$ as described in Example 2, after preparing a suspension free of air bubbles, by molding and vulcanizing for three hours at 90° C.

EXAMPLE 9

Supporting rings having the dimensions of Example 8 are injection-molded from a terephthalate basis thermoplastic polyether ester elastomer.

These supporting rings are combined to form vaginal rings having a ring cross section diameter of 10.2 mm. by inserting the drug-containing inner and outer rings described in Example 8.

EXAMPLE 10

A supporting ring designed for receiving two drug-containing rings having an outer diameter of 3 cm. and an inner diameter of 2 cm. is produced, as indicated in Example 2, from a dimethylpolysiloxane molding composition ("SILASTIC" 4600, Dow Corning). The spacing between the pocket-like recesses of this supporting ring from the outer to the inner ring is 3.1 mm. The drug-containing outer ring has a diameter of 2 mm. and is prepared as indicated in Example 1 from a d-norgestrel suspension in the LTV organopolysiloxane two-component molding composition $C_1$. The drug-containing inner ring has a diameter of 0.5 mm. and is prepared as described in Example 9 from an ethynylestradiol suspension in the LTV organopolysiloxane two-component molding composition $C_3$ as disclosed in Example 2. The drug-containing rings are inserted in the supporting ring; all three rings together form a vaginal ring for use in animals.

EXAMPLE 11

Supporting rings having an outer diameter of 4.2 cm. and an inner diameter of 3.0 cm. are formed with two pocket-like recesses for receiving the outer and inner rings containing the active agent. The outer ring has a diameter of 2.5 mm. and the inner ring has a diameter of 0.5 mm., with a spacing between the pocket-like recesses of 3.8 mm. The supporting rings are prepared from a homogeneous mixture of 31.0 g. of highly disperse silicon dioxide in the catalyzed LTV silicone elastomer baase A and initially vulcanized by heating for 5 minutes to 130° C. The drug-containing vaginal ring is manufactured by molding, in a second process step, onto the initially vulcanized supporting ring. The outer molded ring contains d-norgestrel in the LTV organopolysiloxane two-component molding composition $C_1$ (as described in Example 1) and the inner molded ring contains ethynylestradiol in the LTV organopolysiloxane two-component molding composition $C_2$ (also described in Example 1). This composite is initially vulcanized for 5 minutes by heating to 120° C. and then heated for two hours at 110° C. The vulcanizate is sterilized by heating for 30 minutes in pressurized steam and is then packaged under sterile conditions.

EXAMPLE 12

A supporting ring is produced from a dimethylpolysiloxane molding composition ("SILASTIC" 4600, Dow Corning) by molding, 5 minutes of initial vulcanization at 150° C. and 1.5 hours of vulcanizing at 120° C., this supporting ring having the following dimensions: outer diameter, 6 cm.; inner diameter, 4.2 cm.; and spacing between the pocket-like recesses for receiving the drug-containing outer and inner rings, 5.3 mm.

Into this supporting ring are inserted an outer ring having a diameter of 4 mm., containing metronidazole and nystatin and an inner ring having a diameter of 1 mm. and containing estriol. The outer ring can readily be separated by the female patient from the application unit after using the vaginal ring for 1 week. The remaining, estriol-containing vaginal ring is intended for usage over a period of several weeks.

The drug-containing outer ring, 4 mm. in diameter, is molded from a homogeneous mixture of 30.0 g. of micronized 1β-(hydroxyethyl)-2-methyl-5-nitroimidazole (metronidazole), 30.0 g. of micronized nystatin, 2.0 g. of highly disperse hydrophobic silicon dioxide and 38.0 g. of the LTV organopolysiloxane two-component molding composition $C_4$ described in Example 2. This ring is initially vulcanized for a period of 5 minutes at 100° C. and then for 4 hours at 80° C.

The drug-containing inner ring, having a diameter of 1 mm., is formed from a suspension of 55.0 g. of micronized estriol in 45.0 g. of LTV organopolysiloxane two-component molding composition $C_3$ disclosed in Example 2 and vulcanized by three hours of heating at 95° C.

This vaginal ring is intended for the treatment of trichomoniasis.

EXAMPLE 13

A supporting ring is prepared from dimethylpolysiloxane molding composition ("SILASTIC" 4600, Dow Corning) by molding, 5 minutes of initial vulcanizing at 150° C., and 1.5 hours of vulcanizing at 120° C., this supporting ring having the following dimensions: outer diameter, 6 cm.; inner diameter, 4.2 cm.; and spacing between the pocket-like recesses for receiving the d-norgestrel-containing outer and inner rings, 5.6 mm.

d-Norgestrel-containing rings having a diameter of 4 mm. (outer ring) and a diameter of 1 mm. (inner ring) are made from a suspension of 25.0 g. of micronized d-norgestrel, 12.0 g. of highly disperse silicon dioxide in 63.0 g. of the LTV organopolywiloxane two-component molding composition $C_4$ described in Example 2, initially vulcanized by heating for 10 minutes to 115° C. and subsequently completely vulcanized by heating for three hours at 100° C. The vulcanizates are extracted successively for 90 minutes with 96% ethanol, then again for 30 minutes with 96% ethanol, 60 minutes with 70% ethanol and 30 minutes with 50% ethanol at room temperature, and are thereafter air-dried. The d-norgestrel-containing rings, consisting of an envelope with a low d-norgestrel content on a d-norgestrel-enriched core, are formed into a vaginal ring by insertion into the supporting ring.

EXAMPLE 14

A supporting ring is prepared from a dimethylpolysiloxane molding composition ("SILASTIC" 4600, Dow Corning) as described in Example 13, with the dimensions set forth therein. Estriol-containing outer and inner rings are made from a suspension of 20.0 g. of micronized estriol and 15.0 g. of highly disperse silicon dioxide in the LTV organopolysiloxane two-component molding composition $C_4$ described in Example 2, following the method indicated in Example 13; the rings are partially extracted with ethanol as likewise described therein. The estriol-containing outer ring and the inner ring are inserted in the supporting ring, forming a vaginal ring having a ring cross section diameter of 10.3 mm.

EXAMPLE 15

A supporting ring is prepared from dimethylpolysiloxane molding composition ("SILASTIC" 4600, Dow Corning) by molding, 5 minutes of initial vulcanizing at 150° C., and 1 hour of vulcanizing at 120° C., this supporting ring having the following dimensions: outer diameter, 6 cm.; inner diameter, 4.2 cm.; and spacing between the pocket-like recess for receiving the outer ring and the inner edge of the supporting ring, 6.5 mm.

A d-norgestrel-containing outer ring having a cross section in the shape of a circular segment and a diameter of 2.5 mm. is inserted in this supporting ring. The d-norgestrel-containing outer ring is prepared from a suspension of 20.0 g. of d-norgestrel and 18.0 g. of highly disperse silicon dioxide in 62.0 g. of the LTV organopolysiloxane two-component molding composition $C_3$ by molding and two hours of vulcanizing at 100° C. The composition of the LTV organopolysiloxane two-component molding composition $C_3$ is that of Example 2.

EXAMPLE 16

A supporting ring is prepared from a dimethylpolysiloxane molding composition ("SILASTIC" 4600, Dow Corning) by molding, 5 minutes of initial vulcanization at 150° C. and 1.5 hours of vulcanization at 120° C., this supporting ring having the following dimensions: outer diameter, 6 cm.; inner diameter, 4.2 cm.; and spacing between the pocket-like recess for receiving the drug-containing inner ring and the outer edge of the supporting ring, 8.1 mm.

An estriol-containing inner ring of a diameter of 1.5 mm. is inserted in this supporting ring. This drug-containing inner ring is molded from a suspension of 55.0 g. of micronized estriol in 45.0 g. of the LTV organopolysiloxane two-component molding composition $C_3$ described in Example 2 and vulcanized by heating for three hours to 95° C.

EXAMPLE 17

A vaginal ring containing d-norgestrel and ethynylestradiol having an outer diameter of 60 mm. and an inner diameter of 42 mm. is produced with the use of the multicomponent injection-molding technique from three components as a composite vulcanizate which is vulcanized at 100° C. for one hour. Component 1 is a homogeneous mixture of 26 parts by weight of highly disperse silicon dioxide, 3 parts by weight of highly disperse magnesium oxide and 71 parts by weight of catalyzed LTV silicone elastomer base ("SILOPREN" 3008, Bayer).

Component 2 consists of a mixture of 24 parts by weight of highly disperse silicon dioxide, 8 parts by weight of micronized d-norgestrel and 68 parts by weight of catalyzed LTV silicone elastomer base ("SILOPREN" 3008, Bayer).

Component 3 contains, in 100 parts by weight, 10 parts by weight of micronized ethynylestradiol, 21 parts by weight of an LTV organopolysiloxane molding composition comprising 75 parts by weight of a bilaterally vinyl-terminated polydimethylsiloxane having a viscosity of 100 centistokes at 25° C.; 25 parts by weight of a copolymer composed of 40 molar percent $SiO_2$ units, 45 molar percent $(CH_3)_3SiO_{0.5}$ units and 15 molar percent $Vi(CH_3)_2SiO_{0.5}$ units; 8 parts by weight of an Si—H component consisting of 16.6 molar percent $(CH_3)_3SiO_{0.5}$ units, 33.4 molar percent $(CH_3)_2SiO$ units and 50.0 molar percent $CH_3HSiO$ units; and 10 p.p.m. of platinum (based on the total mixture) in the form of a 2% solution of $H_2PtCl_6$ in isopropanol.

Within the composite vulcanizate, component 1 forms a ring having an ellipsoidal cross section wherein, on the outer and inner edges, the drug-containing components 2 and 3 are vulcanized so that the vaginal ring in total has a circular cross section with a radius of curvature of 4.5 mm. on the outer edge. Component 2 has a maximum layer thickness of 2 mm. and is vulcanized along a circular arc section of 2.5 mm., encompassing the ring. Component 3 is vulcanized in a maximum layer thickness of 1.5 mm. with an expansion of 1.5 mm., surrounding the ring on all sides.

EXAMPLE 18

A vaginal ring is produced from the three components 1–3 described in Example 17 as a composite vulcanizate with the same dimensions, but wherein the drug-free component 1 is combined with methylene chloride so that component 1 evaporates during the injection-molding step and/or during the vulcanizing process and forms a closed-cell foam.

EXAMPLE 19

A vaginal ring is prepared with the dimensions disclosed in Example 17 from three components in the form of a composite vulcanizate with the use of the multicomponent injection-molding technique. Component 1 is a mixture of 24 parts by weight of highly disperse silicon dioxide and 73 parts by weight of LTV silicone elastomer composition ("SILOPREN" 0028, Bayer).

Component 2 is a mixture of 4.8 parts by weight of micronized d-norgestrel, 22.4 parts by weight of highly disperse silicon dioxide and 72.8 parts by weight of the organopolysiloxane two-component molding composition described in Example 17.

Component 3 contains 10 parts by weight of micronized ethynylestradiol and 22 parts by weight of highly disperse silicon dioxide in 68 parts by weight of an LTV organopolysiloxane two-component molding composition containing 75 parts by weight of a bilaterally vinyl-terminated polydimethylsiloxane having a viscosity of 1000 centistokes at 25° C.; 25 parts by weight of a copolymer composed of 40 molar percent $SiO_2$ units, 45 molar percent $(CH_3)_3SiO_{0.5}$ units and 15 molar percent $Vi(CH_3)_2SiO_{0.5}$ units; 8 parts by weight of an Si-H component consisting of 16.6 molar percent $(CH_3)_3SiO_{0.5}$ units, 33.4 molar percent $(CH_3)_2SiO$ units and 50.0 molar percent $CH_3HSiO$ units; 30 p.p.m. of platinum (based on the total mixture) in the form of a 1% solution of $Pt(CO)_2Cl_2$ in an open-chain dimethylpolysiloxane containing 12 molar percent vinyl groups; and 5 parts by weight, based on the parts by weight of platinum, of Cu(II) ions.

From the three aforementioned components, a composite vulcanizate is produced in the form of superimposed rings by 75 minutes of vulcanizing at 120° C. In this composite vulcanizate, component 1 determines the configuration and has an almost circular cross section. On the flattened outer edge of the ring, consisting of drug-free component 1, component 2 is vulcanized in a width of 3 mm. with a maximum layer thickness of 2.0 mm. over 120 mm. of the outer edge of the ring, and component 3 is vulcanized in a width of 2 mm. with a maximum layer thickness of 2.5 mm. over the remaining length of the outer edge.

EXAMPLE 20

A vaginal ring is prepared as a composite vulcanizate by analogy to Example 19. Component 2, containing d-norgestrel, is applied in a width of 2.5 mm. with a layer thickness of maximally 3 mm. continuously along the outer edge of component 1.

EXAMPLE 21

A vaginal ring containing ethynylestradiol and d-norgestrel is produced by the multicomponent injection-molding method from components 1–3 described in detail in Example 19 by composite vulcanization at 120° C. The resultant composite vulcanizate has a circular cross section, carrying along the outer edge component 2 containing d-norgestrel, extending continuously with a maximum layer thickness of 2.0 mm and a width of 2.5 mm. On the inner side of the ring, component 3 containing ethynylestradiol is affixed over a length of 30 mm. with a width of 2.0 mm. and a thickness of about 2.5 mm.

What is claimed is:

1. A composite vaginal ring containing a safe and effective amount of a pharmaceutically active medicament, consisting essentially of:
    (a) a supporting, medicament-free vaginal ring consisting essentially of a physiologically acceptable synthetic resin and having a continuous encircling pocket-like indentation along the inner edge of the annular surface along the central plane thereof adapted to mate with a corresponding smaller, medicament-containing inner encircling annular minor vaginal ring segment; and
    (b) a smaller, vaginal medicament-containing inner encircling annular minor vaginal ring adapted to mate with the continuous encircling pocket-like indentation in the modified annular surface of said supporting, medicament-free vaginal ring along the central plane thereof and consisting essentially of a safe and effective amount of a pharmaceutically active nonionic, lipophilic vaginal drug dissolved or uniformly suspended in an elastomeric, cross-linked LTV linear dimethylpolysiloxane resin.

2. A vaginal ring according to claim 1, wherein said minor ring segment is vulcanized onto said major supporting ring.

3. A vaginal ring according to claim 1, wherein said LTV resin component consists essentially of a nontoxic pharmaceutical composition adapted for implantation into a human or animal body to provide a constant, uniform drug release rate over a time interval of several months or years, being substantially free of peroxide, acetic acid and metal salts of carboxylic acids and consisting essentially of a homogeneous mixture of:
    (a) 85–95, preferably 89–91, parts by weight of an LTV linear dimethylpolysiloxane resin containing 0.05–0.5 molar percent of methylvinylsiloxane units, having a molecular weight of 20,000–50,000 and containing an average of 1.58–2.02 monovalent hydrocarbon residues per silicone atom;

(b) correspondingly 15–5, preferably 11–9, parts by weight of a cross-linking composition consisting essentially of a dimethylpolysiloxane cross-linking agent substantially free of methylvinylsiloxane units, having a molecular weight of 500–1000 and containing 1–3 Si—H bonds per molecule;

(c) a catalytic amount of a noble-metal based cross-linking catalyst; and (d) a pharmaceutically active amount of a nonionic, lipophilic drug dissolved or uniformly suspended in said composition.

4. A vaginal ring according to claim 1, wherein said LTV resin component consists essentially of preferably 85–89 parts by weight of component (a) preferably 5–6 parts by weight of component (b); together with 5–10 parts by weight of a dimethylpolysiloxane resin having a molecular weight of 10,000–40,000 and having 0.2–1.5 molar percent methylvinylsiloxane units as an auxiliary cross-linking agent.

5. A vaginal ring according to claim 1, wherein said LTV resin component consists essentially of (a) 20–100 parts by weight of an organopolysiloxane having a viscosity of 500–200,000 centistokes (at 25° C.) and having the general formula wherein
R is lower alkyl (preferably methyl) and/or aryl of up to 10 carbon atoms, and
n is an integer from 200–1600;

(b) 0–50 parts by weight of an organopolysiloxane copolymer consisting essentially of:
(i) $(R')_3SiO_{0.5}$ units,
(ii) $(R')_2(Vi)SiO_{0.5}$ units, and
(iii) $SiO_2$ units, wherein
Vi is a vinyl group and R' is a monovalent organic residue which does not contain any unsaturated groups, and at least 50% of R' is methyl, and
wherein the ratio of a+b/c is 0.4–1.5 (preferably 0.6–1.0) and the ratio of b/c is 0.02–0.5 (preferably 0.05–0.15);

(c) 5–15 parts by weight of an organohydrogen polysiloxane of the general formula wherein
R" is a monovalent organic residue which has no unsaturated groups, a and b are each positive numbers; the ratio of a:b is 0.5–10 (preferably 1.0–5); the sum of a+b is 1–2.5; and wherein at least three hydrogen atoms bound to different Si atoms are present per molecule; which component contain 50–500 molar percent, based on the unsaturated end groups in components (a) and (b) of vinyl groups attached to SiH; and (d) a catalytic amount of platinum or a platinum compound.

6. A vaginal ring according to claim 1, wherein said major supporting ring is composed of an elastomeric, cross-linked LTV linear dimethylpolysiloxane resin.

7. A vaginal ring according to claim 1, wherein said drug is a steroid hormone.

8. A vaginal ring according to claim 8, wherein said drug is at least one steroid hormone having progestational or estrogenic activity.

9. A vaginal ring according to claim 1, wherein the major supporting ring is a closed-cell foam.

10. A vaginal ring according to claim 10, wherein said major supporting ring is composed of an elastomeric, cross-linked LTV linear dimethylpolysiloxane resin.

11. A vaginal ring according to claim 1, wherein said drug is an antiprotozoal medicament.

12. A vaginal ring according to claim 1, wherein the exposed portion of said minor ring segment is circular in cross-section.

13. A vaginal ring according to claim 12, wherein the entire minor ring segment is circular in cross-section.

14. A vaginal ring according to claim 1, wherein supporting, medicament-free ring (a) also has a continuous encircling pocket-like indentation along the outer edge of the annular surface along the central plane thereof adapted to mate with a corresponding smaller, medicament-containing outer encircling annular minor vaginal ring segment; and which also contains (c) a smaller, vaginal medicament-containing outer encircling annular minor vaginal ring adapted to mate with the continuous encircling pocket-like indentation in the modified outer annular surface of said supporting, medicament-free vaginal ring along the central plane thereof and consisting essentially of a safe and effective amount of a pharmaceutically active nonionic, lipophilic vaginal drug dissolved or uniformly suspended in an elastomeric, crosslinked LTV linear dimethylpolysiloxane resin;

whereby the composite ring contains both inner and outer minor ring segments along the central plane of said major supporting ring.

15. A vaginal ring according to claim 14, wherein one of said minor ring segments contains a progestationally active steroid drug and the other of said ring segments contains an estrogenically active steroid drug.

16. A vaginal ring according to claim 15, wherein the major supporting ring is a closed-cell foam composed of an elastomeric, cross-linked LTV linear dimethylpolysiloxane resin.

17. A vaginal ring according to claim 16 dimensioned for insertion into a human female vagina.

18. A vaginal ring according to claim 17 further comprising an antiprotozoal drug in a portion of at least one of said minor rings.

19. A vaginal ring according to claim 18, wherein the exposed portion of said minor ring segments are circular in cross-section.

* * * * *